US012662551B2

(12) United States Patent
Da et al.

(10) Patent No.: US 12,662,551 B2
(45) Date of Patent: Jun. 23, 2026

(54) MONOCLONAL ANTIBODY FOR DETECTION OF CAR-T CELLS, KIT AND APPLICATION

(71) Applicant: Suzhou Bioswan Laboratories, Co., Ltd., Suzhou (CN)

(72) Inventors: Liang Da, Suzhou (CN); Guowei Wei, Suzhou (CN); Xin Chen, Suzhou (CN); Dongge Feng, Suzhou (CN); Wei He, Suzhou (CN); Xuejun Yu, Suzhou (CN)

(73) Assignee: BIOSWAN LABORATORIES, CO., LTD., Shanghai (CN)

( * ) Notice: Subject to any disclaimer, the term of this patent is extended or adjusted under 35 U.S.C. 154(b) by 1065 days.

(21) Appl. No.: 17/779,608

(22) PCT Filed: Nov. 25, 2020

(86) PCT No.: PCT/CN2020/131564
§ 371 (c)(1),
(2) Date: May 25, 2022

(87) PCT Pub. No.: WO2021/104326
PCT Pub. Date: Jun. 3, 2021

(65) Prior Publication Data
US 2023/0027639 A1     Jan. 26, 2023

(30) Foreign Application Priority Data
Nov. 25, 2019    (CN) .......................... 201911166683.7

(51) Int. Cl.
*C07K 16/42*     (2006.01)
*G01N 33/569*     (2006.01)
*G01N 33/577*     (2006.01)

(52) U.S. Cl.
CPC ....... *C07K 16/42* (2013.01); *G01N 33/56966* (2013.01); *G01N 33/56972* (2013.01); *G01N 33/577* (2013.01); *C07K 2317/565* (2013.01); *C07K 2317/622* (2013.01)

(58) Field of Classification Search
CPC .......... G01N 33/56966; G01N 33/557; G01N 33/56972; C07K 16/42; C07K 16/2803
See application file for complete search history.

(56) References Cited

U.S. PATENT DOCUMENTS

2018/0086846 A1*   3/2018   Wiltzius ............. C07K 14/7051

FOREIGN PATENT DOCUMENTS

| CN | 107793478 A | 3/2018 |
| CN | 108490174 A | 9/2018 |
| CN | 108508200 A | 9/2018 |
| CN | 110325209 A | 10/2019 |
| CN | 110894238 A | 3/2020 |
| WO | 2014190273 A1 | 11/2014 |
| WO | 2018064205 A1 | 4/2018 |

OTHER PUBLICATIONS

Bipulendu Jena et al. Chimeric Antigen Receptor (CAR)-Specific Monoclonal Antibody to Detect CD19-Specific T cells in Clinical Trials. PLOS ONE 8 (3) e57838: 1-12 (Mar. 2013).*
Int'l Search Report issued Feb. 24, 2022 in Int'l Application No. PCT/CN2020/131564.
Jena et al, "Chimeric Antigen Receptor (CAR)-Specific Monoclonal Antibody to Detect CD19-Specific T Cells in Clinical Trials," PLOS ONE, vol. 8, No. 3, Article E57838, pp. 1-12 (2013).
European Search Report issued Jan. 2, 2024 in Int'l Application No. PCT/CN2020/131564.

* cited by examiner

*Primary Examiner* — Gailene Gabel
(74) *Attorney, Agent, or Firm* — Panitch Schwarze Belisario & Nadel LLP

(57)     ABSTRACT

A monoclonal antibody used for specifically binding to CAR molecules, which is characterized in that the monoclonal antibody comprises a light chain and a heavy chain, the light chain comprises CDR regions having an amino acid sequence as shown in SEQ ID NO: 1-3, and the heavy chain comprises CDR regions having an amino acid sequence as shown in SEQ ID NO: 5-7. By using the described monoclonal antibody or a CAR-T cell detection kit, the steps of CAR-T cell detection are simple, detection time is short, and the detection results are stable. An anti-FMC63 ScFv antibody can reduce the cost of detecting universal anti-CD19 CAR-T cells.

5 Claims, 3 Drawing Sheets

Specification includes a Sequence Listing.

Isotype: P1 cell population

Antibody in Experimental group: P1 cell population          CD19 protein in Control group: P1 cell population Isotype: P1 cell population ①    CAR-T + K562
②    CAR-T + CD19⁺ K562
③    CAR-T + CD19⁺ K562 + mAb 25 μg/ml
④    CAR-T + CD19⁺ K562 + mAb 5 μg/ml

SEQUENCE LISTING

<160> NUMBER OF SEQ ID NOS: 11

<210> SEQ ID NO 1
<211> LENGTH: 11
<212> TYPE: PRT
<213> ORGANISM: Artificial Sequence
<220> FEATURE:
<223> OTHER INFORMATION: VL CDR1

<400> SEQUENCE: 1

Arg Ala Ser Gln Asp Ile Ser Asn Tyr Leu Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: VL CDR2

<400> SEQUENCE: 2

```
Tyr Thr Ser Arg Leu Arg Ser
1               5

<210> SEQ ID NO 3
<211> LENGTH: 9
<212> TYPE: PRT
<213> ORGANISM: Artificial Sequence
<220> FEATURE:
<223> OTHER INFORMATION: VL CDR3

<400> SEQUENCE: 3

Gln Gln Gly Asp Thr Leu Pro Tyr Thr
1               5

<210> SEQ ID NO 4
<211> LENGTH: 107
<212> TYPE: PRT
<213> ORGANISM: Artificial Sequence
<220> FEATURE:
<223> OTHER INFORMATION: Variable region of light chain

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Ala Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Asn
            100                 105

<210> SEQ ID NO 5
<211> LENGTH: 7
<212> TYPE: PRT
<213> ORGANISM: Artificial Sequence
<220> FEATURE:
<223> OTHER INFORMATION: VH CDR1

<400> SEQUENCE: 5

Gly Tyr Ser Phe Thr Asp Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: VH CDR2

<400> SEQUENCE: 6

Asp Pro Tyr Asn Gly Gly
1               5

<210> SEQ ID NO 7
<211> LENGTH: 9
<212> TYPE: PRT
<213> ORGANISM: Artificial Sequence
```

-continued

```
<220> FEATURE:
<223> OTHER INFORMATION: VH CDR3

<400> SEQUENCE: 7

Thr Tyr Asp Asn Tyr Glu Phe Ala Tyr
1               5

<210> SEQ ID NO 8
<211> LENGTH: 118
<212> TYPE: PRT
<213> ORGANISM: Artificial Sequence
<220> FEATURE:
<223> OTHER INFORMATION: Variable region of heavy chain

<400> SEQUENCE: 8

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ser Phe Thr Asp Tyr
                20                  25                  30

Thr Met Tyr Trp Val Lys Gln Ser His Gly Lys Ser Leu Glu Trp Ile
            35                  40                  45

Gly Tyr Ile Asp Pro Tyr Asn Gly Gly Thr Asn Tyr Ser Gln Arg Phe
        50                  55                  60

Lys Gly Lys Ala Thr Leu Thr Val Asp Lys Ser Ser Ser Thr Ala Phe
65                  70                  75                  80

Met His Leu Asn Ser Leu Pro Ser Glu Asp Ser Ala Val Tyr Tyr Cys
                85                  90                  95

Ala Asn Thr Tyr Asp Asn Tyr Glu Phe Ala Tyr Trp Gly Gln Gly Thr
                100                 105                 110

Leu Val Thr Val Ser Ala
            115

<210> SEQ ID NO 9
<211> LENGTH: 279
<212> TYPE: PRT
<213> ORGANISM: Artificial Sequence
<220> FEATURE:
<223> OTHER INFORMATION: Recombinant protein of non-antiCD19 antigen

<400> SEQUENCE: 9

Met Pro Thr Pro Leu Val His Pro His Leu Pro Ile Ser Ser Pro Arg
1               5                   10                  15

Val Ser Pro Phe Pro Pro Pro Ala Phe Gln Lys Ala Ser Ser Ile Val
                20                  25                  30

Tyr Lys Lys Glu Gly Glu Gln Val Glu Phe Ser Phe Pro Leu Ala Phe
            35                  40                  45

Thr Val Glu Lys Leu Thr Gly Ser Gly Glu Leu Trp Trp Gln Ala Glu
        50                  55                  60

Arg Ala Ser Ser Ser Lys Ser Trp Ile Thr Phe Asp Leu Lys Asn Lys
65                  70                  75                  80

Glu Val Ser Val Lys Arg Val Thr Gln Asp Pro Lys Leu Gln Met Gly
                85                  90                  95

Lys Lys Leu Pro Leu His Leu Thr Leu Pro Gln Ala Leu Pro Gln Tyr
                100                 105                 110

Ala Gly Ser Gly Asn Leu Thr Leu Ala Leu Glu Ala Lys Thr Gly Lys
            115                 120                 125

Leu His Gln Glu Val Asn Leu Val Val Met Arg Ala Thr Gln Leu Gln
        130                 135                 140
```

```
Lys Asn Leu Thr Cys Glu Val Trp Gly Pro Thr Ser Pro Lys Leu Met
145                 150                 155                 160

Leu Ser Leu Lys Leu Glu Asn Lys Glu Ala Lys Val Ser Lys Arg Glu
                165                 170                 175

Lys Ala Val Trp Val Leu Asn Pro Glu Ala Gly Met Trp Gln Cys Leu
                180                 185                 190

Leu Ser Asp Ser Gly Gln Val Leu Leu Glu Ser Asn Ile Lys Val Leu
                195                 200                 205

Pro Thr Trp Ser Thr Pro Val Gln Pro Met Ala Leu Ile Val Leu Gly
                210                 215                 220

Gly Val Ala Gly Leu Leu Leu Phe Ile Gly Leu Gly Ile Phe Phe Cys
225                 230                 235                 240

Val Arg Cys Arg His Arg Arg Arg Gln Ala Glu Arg Met Ser Gln Ile
                245                 250                 255

Lys Arg Leu Leu Ser Glu Lys Lys Thr Cys Gln Cys Pro His Arg Phe
                260                 265                 270

Gln Lys Thr Cys Ser Pro Ile
                275

<210> SEQ ID NO 10
<211> LENGTH: 242
<212> TYPE: PRT
<213> ORGANISM: Artificial Sequence
<220> FEATURE:
<223> OTHER INFORMATION: Recombinant protein of FMC63 scFv

<400> SEQUENCE: 10

Glu Val Lys Leu Gln Glu Ser Gly Pro Gly Leu Val Ala Pro Ser Gln
1                   5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
                35                  40                  45

Gly Val Ile Trp Gly Ser Glu Thr Thr Tyr Tyr Asn Ser Ala Leu Lys
                50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser Gly Gly Gly Gly Ser Gly Gly Gly
                115                 120                 125

Gly Ser Gly Gly Gly Gly Ser Asp Ile Gln Met Thr Gln Thr Thr Ser
                130                 135                 140

Ser Leu Ser Ala Ser Leu Gly Asp Arg Val Thr Ile Ser Cys Arg Ala
145                 150                 155                 160

Ser Gln Asp Ile Ser Lys Tyr Leu Asn Trp Tyr Gln Gln Lys Pro Asp
                165                 170                 175

Gly Thr Val Lys Leu Leu Ile Tyr His Thr Ser Arg Leu His Ser Gly
                180                 185                 190

Val Pro Ser Arg Phe Ser Gly Ser Gly Ser Gly Thr Asp Tyr Ser Leu
                195                 200                 205

Thr Ile Ser Asn Leu Glu Gln Glu Asp Ile Ala Thr Tyr Phe Cys Gln
                210                 215                 220
```

-continued

```
Gln Gly Asn Thr Leu Pro Tyr Thr Phe Gly Gly Gly Thr Lys Leu Glu
225                 230                 235                 240

Ile Thr

<210> SEQ ID NO 11
<211> LENGTH: 15
<212> TYPE: PRT
<213> ORGANISM: Artificial Sequence
<220> FEATURE:
<223> OTHER INFORMATION: Linking Peptide

<400> SEQUENCE: 11

Gly Gly Gly Gly Ser Gly Gly Gly Gly Ser Gly Gly Gly Gly Ser
1               5                   10                  15
```

1

MONOCLONAL ANTIBODY FOR DETECTION OF CAR-T CELLS, KIT AND APPLICATION

CROSS-REFERENCE TO RELATED APPLICATIONS

This application is a Section 371 of International Application No. PCT/CN2020/131564, filed Nov. 25, 2020, which was published in the Chinese language on Jun. 3, 2021, under International Publication No. WO 2021/104326 A1, which claims priority under 35 U.S.C. § 119 (b) to Chinese Application No. 201911166683.7, filed Nov. 25, 2019, the disclosure of each of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688457_110US_Sequence_Listing", creation date of May 24, 2022, and having a size of 8.24 KB (8,438 bytes). The sequence listing submitted via EFS-Web is part of the specification and is herein incorporated by reference in its entirety.

TECHNICAL FIELD

The present invention is related to the field of molecular biology, and more particularly to a monoclonal antibody, kit and application for detection of CAR-T cells.

BACKGROUND

CD19 molecule is one of the surface markers of B cells, also known as B4 or Leu-12. CD19 is a transmembrane glycoprotein. CD19 molecule expression starts from bone marrow B cells and continues throughout B cell maturation. CD19 CAR-T (chimeric antigen receptor T) cells are artificially engineered T cells, wherein the genetic engineering modification methods are used to make CAR (chimeric antigen receptor) recognizing CD19, which is called anti-CD19 CAR, be expressed on the surface of T cells, so that CD19 CAR-T cells can recognize tumor B cells expressing CD19. At present, CD19 CAR-T cells have been used in clinic for treating B-cell malignant hematological tumors with CD19 positive expression.

There are many difficulties in the clinical application of CD19 CAR-T cells. One of the difficulties is that the cost of CD19 CAR-T cell detection is too high. Because the anti-CD19 CAR expressed on the surface of CD19 CAR-T is used to identify CD19 molecules, the traditional detection of CD19 CAR-T is using CD19 molecules. However, there exists problem of the low specificity, complex test conditions and high dosage of added antigen protein when human CD19 antigen is to detect anti-CD19 CAR on the surface of CD19 CAR-T cells. In addition to this method, there are also methods used for the detection of clinical CAR-T cell infection efficiency. QPCR detection method is used for targets other than CD19. This method can not accurately quantify the infection efficiency. Therefore, it is necessary to develop a new CAR-T cell detection reagent.

SUMMARY OF INVENTION

In order to solve the existing problem, in the present invention, it provides a monoclonal antibody, kit and application for detection of CAR-T cells.

To achieve the above object, the present invention is implemented by the following technical solutions:

In the first aspect of the present invention, it provides a monoclonal antibody, which comprises a light chain and a heavy chain, wherein the light chain comprises CDR regions whose amino acid sequences are shown in SEQ ID NOs: 1-3, and the heavy chain comprises CDR regions whose amino acid sequences are shown in SEQ ID NOs: 5-7.

In the second aspect of the present invention, it provides a polynucleotide, which encodes a variable region of the heavy chain and/or a variable region of the light chain or a full-length amino acid of the aforementioned monoclonal antibody specifically binding to a CAR molecule.

In the third aspect of the present invention, it provides a construct, wherein the construct is constructed by inserting the aforementioned polynucleotide into a polyclonal site of an expression vector.

In the fourth aspect of the present invention, it provides a host cell, which comprises the aforementioned construct, or having the aforementioned polynucleotide integrated into a chromosome thereof.

In the fifth aspect of the present invention, it provides a method for preparing the aforementioned monoclonal antibody specifically binding to a CAR molecule, which comprises the following steps: culturing the aforementioned host cell to express the monoclonal antibody under a condition suitable for expressing the monoclonal antibody, and purifying and isolating the monoclonal antibody.

In the sixth aspect of the present invention, it provides a use of the aforementioned monoclonal antibody for preparing a CAR-T cell detection agent.

In the seventh aspect of the present invention, it provides a CAR-T cell detection kit, which comprises a capture ligand and a detection ligand, wherein the capture ligand comprises a first ligand and a first ligand marker which are connected together, wherein the first ligand is the aforementioned monoclonal antibody; and the detection ligand comprises a second ligand used to identify the capture ligand.

In the eighth aspect of the present invention, it provides a use of the aforementioned monoclonal antibody specifically binding to a CAR molecule, the polynucleotide, the construct, the host cell or the CAR-T cell detection kit for detecting CAR-T cells.

In the ninth aspect of the present invention, it provides a method for detecting CAR-T cells, which comprises the steps of:

1) adding the aforementioned monoclonal antibody or the capture ligand of the kit into a sample to be tested, incubating and centrifuging, thereby obtaining a first deposit;

2) adding a detection ligand for identifying the aforementioned monoclonal antibody or the detection ligand of the kit into the first deposit, incubating and centrifuging, thereby obtaining a second deposit;

3) detecting the second deposit by flow cytometry, thereby obtaining the CAR-T cell measurement of the sample to be tested.

Compared with the prior art, the beneficial effects of the present invention comprise:

by using the monoclonal antibody or the CAR-T cell detection kit of the present invention, CAR-T cell detection can be performed with simple detection steps, short detection time, low requirements for cell status, high sensitivity, good distinguishing effects and stable detection results. At present, the anti-CD19 CAR detection using commercial antigens consumes a quite large amount of protein and is expensive (about 120 RMB/ test). The anti-FMC63 ScFv antibody of the present invention can highly reduce the cost of detecting universal anti-CD19 CAR-T cells, wherein the cost is reduced 6 times and is as low as 20 RMB/test.

EMBODIMENTS

Figure 1:
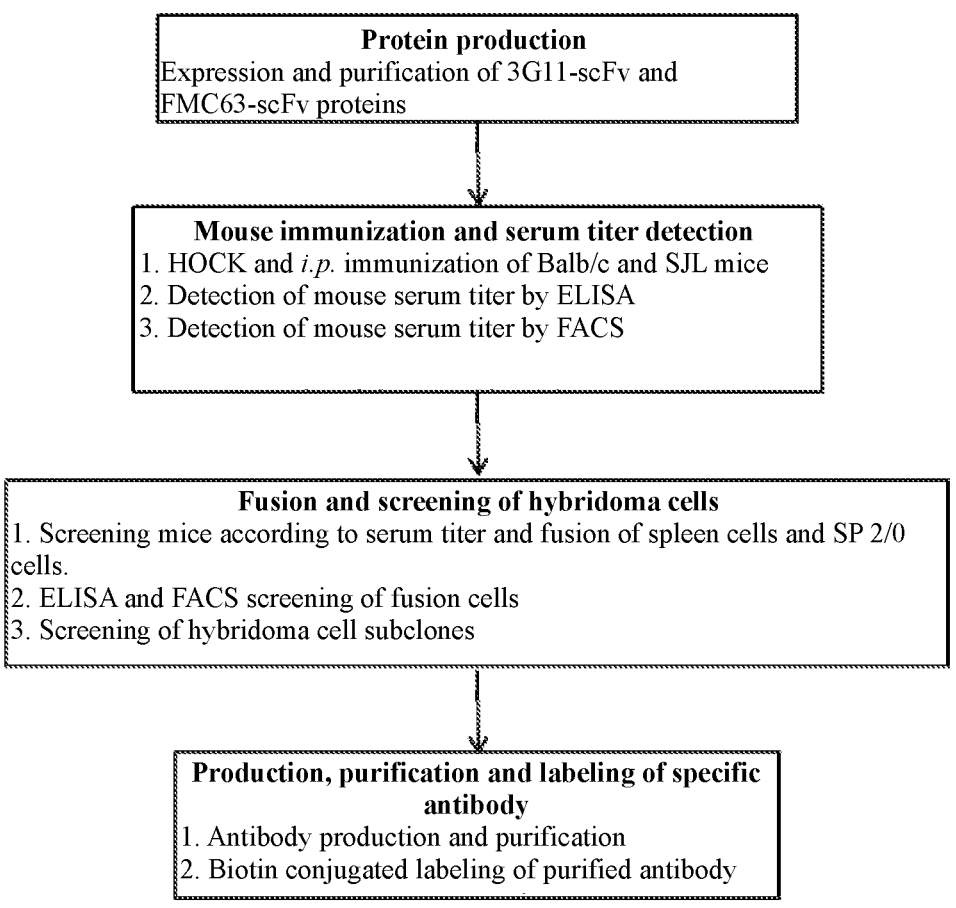
FIG. 1 shows a flowchart of the preparation of the monoclonal antibody of Example 1.

After extensive and intensive research and via a large number of screenings, the inventors have unexpectedly obtained an antibody against FMC63 scFv. Experiments show that, the antibody of the present invention can effectively detect the anti-CD19 CAR expression on surface of CD19 CAR-T cells, with simple detection steps, short detection time, low requirements for cell status, high sensitivity, good distinguishing effects and stable detection results. Moreover, the antibody of the present invention exhibits an excellent blocking effect on CD19 CAR-T cells at low concentration and inhibits the killing effect of CAR-T cells, which indicates that the monoclonal antibody of the present invention has higher sensitivity and better blocking performance. Therefore, it is more suitable for detecting the killing performance of CAR-T cells in which the extracellular binding domain of CAR is FMC63 ScFv, and for quality control. On this basis, the present invention is completed.

The implementations of the present invention will be described below with reference to specific examples. Those skilled in the art may easily understand other advantages and effects of the present invention by the contents disclosed in the present specification. The present invention may also be implemented or applied through other different specific implementations. Various modifications or changes may also be made on the details in the present specification without departing from the spirit of the present invention based on different viewpoints and applications.

Before the implementations according to the present invention is further described, it should be understood that the protection scope of the present invention is not limited to the specific implementations described below. It should also be understood that the terms in the embodiments according to the present invention are used to describe the particular implementations and not to limit the protection scope of the present invention. In the specification and claims of the present invention, unless otherwise stated specifically, the singular forms "a", "an", and "the" include the plural forms.

When the numerical ranges are given by the embodiments, it should be understood that the two endpoints of each numerical range and any numerical value between the two endpoints can be selected, unless otherwise stated herein. Unless otherwise defined, all technical and scientific terms used in the present invention have the same meaning as commonly understood by those skilled in the art. In addition to the specific methods, devices and materials, any methods, devices, and materials of the prior art that are similar or equivalent to the methods, devices, and materials described in the embodiment according to the present invention can also be used to implement the present invention in accordance with the prior art known by those skilled in the art and the description of the present invention.

Unless otherwise stated, the experimental methods, detection methods, and preparation methods disclosed in the present invention employ conventional techniques in molecular biology, biochemistry, chromatin structure and analysis, analytical chemistry, cell culture, recombinant DNA technology and the related fields. These techniques have been well described in the existing literatures.

In the present invention, the term "monoclonal antibody (mAb)" refers to an antibody obtained from a substantially homogeneous population, that is, the individual antibodies contained in the population are the same except for a few possible naturally occurring mutations. Monoclonal antibody targets a single antigen site with high specificity. Moreover, unlike conventional polyclonal antibody preparations (which usually comprises different antibodies targeting different determinants), each monoclonal antibody targets one single determinant on the antigen. In addition to their specificity, the benefit of monoclonal antibodies is that they are synthesized by hybridoma culture and are not contaminated by other immunoglobulins. The modifier "monoclonal" indicates the characteristics of an antibody, which is obtained from a substantially uniform antibody population, and it should not be interpreted as requiring any special method to produce antibodies.

As used herein, the term "antibody" refers to an immunoglobulin molecule usually composed of two pairs of polypeptide chains (each pair has a "light" (L) chain and a "heavy" (H) chain). In a general sense, a heavy chain can be understood as a polypeptide chain with a larger molecular weight in an antibody, and a light chain refers to a polypeptide chain with a smaller molecular weight in an antibody. Light chains can be classified into κ and λ light chains. Heavy chains can generally be classified into μ, δ, γ, α or ε chain, and the isotypes of the antibody are defined as IgM, IgD, IgG, IgA and IgE, respectively. In the light chain and heavy chain, the variable regions and constant regions are connected by a "J" region of about 12 or more amino acids, and the heavy chain also comprises a "D" region of about 3 or more amino acids. Each heavy chain consists of a variable heavy chain (VH) and a constant heavy chain (CH). The heavy chain constant region consists of 3 domains (CH1, CH2 and CH3). Each light chain consists of a light chain variable region (VL) and a light chain constant region (CL). The light chain constant region consists of a domain CL. The constant regions of an antibody can mediate the binding of immunoglobulins to host tissues or factors, including various cells of the immune system (e.g., effector cells) and the first component (C1q) of the classical complement system. The VH and VL regions can also be subdivided into hyper variable regions (called complementarity determining regions (CDR)), interspersed with more conservative regions called framework regions (FR). Each VH and VL is composed of 3 CDRs and 4 FRs arranged in the following order: FR1, CDR1, FR2, CDR2, FR3, CDR3 and FR4 from the amino terminal to the carboxy terminal. The variable regions (VH and VL) corresponding to each heavy chain/ light chain respectively form the antibody binding site. The assignment of amino acids to each region or domain follows the definition of Kabat Sequences of Proteins of Immuno- logical Interest (National Institutes of Health, Bethesda, Md.(1987 and 1991)), or Chothia & Lesk (1987) J. Mol. Biol. 196:901-917; Chothia et al. (1989) Nature 342:878- 883. In particular, the heavy chain may also comprise more than 3 CDRs, for example 6, 9 or 12 CDRs. For example, in the bifunctional antibody of the present invention, the heavy chain may be the C-terminus of the heavy chain of an IgG antibody connecting to the ScFv of another antibody. In this case, the heavy chain has 9 CDRs. The term "antibody" is not limited by any particular method for producing an antibody. For example, it includes, in particular, recombi- nant antibodies, monoclonal antibodies and polyclonal anti- bodies. The antibodies may be antibodies of different iso- types, for example, IgG (e.g., IgG1, IgG2, IgG3 or IgG4 subtypes), IgA1, IgA2, IgD, IgE or IgM antibodies.

The monoclonal antibodies can be prepared using a variety of well known methods in the art. For example, the monoclonal antibodies can be prepared by hybridoma method (first proposed by Kohler et al., Nature, 256:495 (1975)), or recombinant DNA method (U.S. Pat. No. 4,816, 567). The monoclonal antibodies can also be isolated from phage antibody library according to the techniques as dis- closed for example, in Clackson et al., Nature, 352:624-628 (1991) and Marks et al., J. Mol. Biol., 222:581-597 (1991).

As used herein, the term "vector" refers to a nucleic acid vehicle into which a polynucleotide can be inserted. When a vector enables the expression of a protein encoded by an inserted polynucleotide, the vector is referred to as an expression vector. A vector can be introduced into a host cell by transformation, transduction, or transfection, so that the genetic material elements carried by the vector can be expressed in the host cell. Vectors are well known to those skilled in the art and include but are not limited to: plasmids; phagemids; cosmids; artificial chromosomes, such as yeast artificial chromosomes (YAC), bacterial artificial chromo- somes (BAC) or P1-derived artificial chromosomes (PAC); phages such as λ phages or M13 phages and animal viruses. Animal viruses that can be used as vectors include, but are not limited to, retroviruses (including lentiviruses), adeno- viruses, adeno-associated viruses, herpes viruses (such as herpes simplex virus), poxviruses, baculoviruses, papillo- maviruses, and papovaviruses (such as SV40). A vector can contain a variety of elements that control expression, includ- ing, but not limited to, promoter sequence, transcription initiation sequence, enhancer sequence, selection element, and reporter gene. In addition, the vector may contain a replication initiation site.

As used herein, the term "specifically bind" refers to a non-random binding reaction between two molecules, such as a reaction between an antibody and an antigen it targets. In some embodiments, an antibody that specifically binds to an antigen (or an antibody that is specific for an antigen) means that the antibody binds to the antigen with an affinity (Kd) of less than about $10^{-5}$M, such as less than about $10^{-6}$ M, less than about $10^{-7}$ M, less than about $10^{-8}$M, less than about $10^{-9}$M, or less than about $10^{-10}$ M or less. In some embodiments of the present invention, the term "targeting" refers to specific binding.

The monoclonal antibody provided in the present inven- tion for specifically binding to a CAR molecule comprises a light chain and a heavy chain, wherein the light chain comprises CDR regions whose amino acid sequences are as shown in SEQ ID NOs: 1-3, and the heavy chain comprises CDR regions whose amino acid sequences are as shown in SEQ ID NOs: 5-7.

The heavy chain and light chain can be connected with a disulfide bond.

In one embodiment, the amino acid sequence of the light chain variable region of the monoclonal antibody is shown in SEQ ID NO: 4.

In one embodiment, the amino acid sequence of the heavy chain variable region of the monoclonal antibody is shown in SEQ ID NO: 8.

The monoclonal antibody may be murine-derived, human-derived or chimeric, and preferably the monoclonal antibody is murine-derived.

The monoclonal antibody comprises a non-CDR region.

Further, the monoclonal antibody subtype is IgG1, IgG2a, IgG2b, IgG2c or IgG3.

Further, the monoclonal antibody is capable of binding on the scFv domain of CAR molecule.

The polynucleotide provided in the present invention encodes a variable region of the heavy chain and/or a variable region of the light chain or a full-length amino acid of the aforementioned monoclonal antibody specifically binding to a CAR molecule.

The construct is provided in the present invention, wherein the construct is constructed by inserting the afore- mentioned polynucleotide into a polyclonal site of an expression vector.

The expression vector may specifically be a commonly used expression vector familiar to those skilled in the art. The specific expression vectors that may be employed include, but are not limited to, pET series expression vec- tors, pGEX series expression vectors, pcDNA series expres- sion vectors and the like.

The host cell provided in the present invention comprises the aforementioned construct, or has the aforementioned polynucleotide integrated into its chromosome.

Any cell suitable for expression of the expression vector (construct) can be used as the host cell, such as cells of yeast, insects, plants, etc. Preferably, the host cell is a eukaryotic cell, and may use a mammal animal host cell line incapable of generating an antibody. The cell line specifically includes but is not limited to: Chinese hamster ovary cells (CHO), baby hamster kidney cells (BHK, ATCC CCL 10), young rat Sertoli cells, monkey kidney cells (COS cells), monkey kidney CVI cells converted by SV40 (COS-7, ATCC CRL 165 1), human embryo kidney cells (HEK-293 lines), mon- key kidney cells (CVI, ATCC CCL-70), African green monkey kidney cells (VERO-76, ATCC CRL-1587), human cervical cancer cells (HELA, ATCC CCL 2), etc.

The method for preparing the aforementioned monoclonal antibody specifically binding to a CAR molecule is provided in the present invention, which comprises steps of: culturing the aforementioned host cell to express the monoclonal antibody under a condition suitable for expressing the mono- clonal antibody, and purifying and isolating the monoclonal antibody.

After a nucleic acid sequence encoding the antibody of the present invention is obtained, a target antibody may be prepared and produced according to the following method. For example, a vector containing a nucleic acid encoding the target antibody is directly introduced into a host cell, which is cultured under suitable conditions, so that the expression of the encoded antibody is induced. The expression vector and the host cell used in the present invention are all those in the prior art, and can be directly commercially obtained. 10% FBS 1640 culture medium used in a culture process are among various conventional culture media. Those skilled in the art may select applicable 1640 culture medium according to experience for culture under the condition suitable for the growth of the host cell. After the host cell grows to a proper cell density, selected promoters are induced by a proper method (such as temperature conversion or chemical induction), and the cell is further cultured for a period of time. In the above-mentioned method, recombinant polypeptides may be expressed in a cell or on a cell membrane, or secreted out of the cell. Once the monoclonal antibody of the present invention is obtained, the monoclonal antibody may be isolated and purified by various isolation methods based on its physical, chemical and other characteristics. Those methods are well known to those skilled in the art. Examples of those methods include but are not limited to: conventional renaturation treatment, treatment by a protein precipitation agent (a salting out method), centrifugation, permeation, super treatment, super centrifugation, molecular sieve chromatography (gel filtration), adsorption chromatography, ion exchange chromatography, high performance liquid chromatography (HPLC), various other liquid chromatography technologies, and the combination thereof.

In the present invention, it further provides a use of the aforementioned monoclonal antibody for preparing a CAR-T cell detection reagent.

The CAR-T cell detection kit is provided in the present invention, which comprises a capture ligand and a detection ligand, wherein the capture ligand comprises a first ligand and first ligand marker connected together, wherein the first ligand is the aforementioned monoclonal antibody; and the detection ligand comprises a second ligand used to identify the capture ligand.

Further, the capture ligand can bind to the scFv domain of CAR molecule.

In one embodiment, the first ligand marker is selected from biotin or alkaline phosphatase.

In one embodiment, the detection ligand is bound to a fluorescent molecule.

In one embodiment, the second ligand is selected from one or more of streptavidin and IgG (including but not limited to those derived from goats, rats, rabbits, chickens, humans and monkeys and other sources).

In one embodiment, the kit may further comprise one or more selected from the group consisting of 1) support medium; 2) stop solution; 3) dilution; 4) washing solution; 5) blocking solution; 6) negative control; and 7) positive control.

In the kit, the support medium may previously be coated with the capture ligand, or may only be a blank support medium to be coated with the capture ligand before detection by using conventional methods by the operator.

The support medium may have a microporous membrane on the surface in contact with the reagent. Thus, the support medium is a microporous membrane plate. The microporous membrane plate may be any of various microporous membrane plates having common specifications, such as a 96-well membrane plate. More preferably, the support medium is a microporous culture plate covered with PVDF film. Preferably, the support medium has a PVDF film on the surface in contact with the reagent.

The stop solution, dilution, washing solution, blocking solution, negative control and positive control are all common reagents in antibody detection and not limited by specific detection items. Therefore, they can either be optionally added into the kit as needed, or be prepared by the operator or purchased separately.

The wash solution may be a commonly used wash solution in the detection kit, such as phosphate buffer and the like. Concentrated or non-concentrated wash solutions can be selected as required.

The blocking solution may be a blocking solution commonly used to coat microporous membrane plate, such as PBS, acetic acid, methanol, Tween, sucrose, skimmed emulsion, FBS, BSA or casein.

The negative control may be non-antiCD19 antigen recombinant protein (manufacturer: Novus Biologicals, Article Number: NBP2-25199) or IgG.

Alternatively, the sequence of the negative control is shown in SEQ ID NO: 9 as follows:

```
MPTPLVHPHLPISSPRVSPFPPPAFQKASSIVYKKEGEQVEFSFPLAFT

VEKLTGSGELWWQAERASSSKSWITFDLKNKEVSVKRVTQDPKLQMGKK

LPLHLTLPQALPQYAGSGNLTLALEAKTGKLHQEVNLVVMRATQLQKNL

TCEVWGPTSPKLMLSLKLENKEAKVSKREKAVWVLNPEAGMWQCLLSDS

GQVLLESNIKVLPTWSTPVQPMALIVLGGVAGLLLFIGLGIFFCVRCRH

RRRQAERMSQIKRLLSEKKTCQCPHRFQKTCSPI.
```

The positive control may be FMC63 scFv recombinant protein (manufacturer: Novus Biologicals, Article Number: NBP2-52688) or IgG.

Alternatively, the sequence of the positive control is shown in SEQ ID NO: 10 as follows:

```
EVKLQESGPGLVAPSQSLSVTCTVSGVSLPDYGVSWIRQPPRKGLEWLG

VIWGSETTYYNSALKSRLTIIKDNSKSQVFLKMNSLQTDDTAIYYCAKH

YYYGGSYAMDYWGQGTSVTVSSGGGGSGGGGSGGGGSDIQMTQTTSSLS

ASLGDRVTISCRASQDISKYLNWYQQKPDGTVKLLIYHTSRLHSGVPSR

FSGSGSGTDYSLTISNLEQEDIATYFCQQGNTLPYTFGGGTKLEIT.
```

Typically, each reagent in the kit of the present invention is stored separately.

In the present invention, it further provides the use of the aforementioned monoclonal antibody for specifically binding to a CAR molecule, the polynucleotide, the construct, the host cell or the CAR-T cell detection kit for detecting CAR-T cells.

A method for detecting CAR-T cells is provided in the present invention, which comprises the steps of:

1) adding the aforementioned monoclonal antibody or the capture ligand of the kit into a sample to test, incubating and centrifuging, thereby obtaining a first deposit;

2) adding a detection ligand for identifying the aforementioned monoclonal antibody or the detection ligand of the kit into the first deposit, incubating and centrifuging, thereby obtaining a second deposit;

3) detecting the second deposit by flow cytometry, thereby obtaining the CAR+ cell content in the CAR-T cells of the sample to be tested.

Preferably, the method specifically comprises the steps of:
1) mixing the sample to be tested with the first ligand connected with the first ligand marker in flow cytometry buffer, binding for 15-45 minutes at 2-8° C., then performing the first centrifuging, thereby obtaining the first deposit;
2) washing the first deposit and resuspending it with the flow cytometry buffer, adding the detection ligand connected with a fluorescent molecule, binding for 15-45 minutes at 2-8° C., and then performing the second centrifuging, thereby obtaining the second deposit;
3) washing and centrifuging the second deposit, resuspending the obtained deposit with flow cytometry buffer, then detecting with flow cytometry.

Example 1 Obtaining of Hybridoma Cell Lines and Preparation of Monoclonal Antibodies The preparation flow is shown in FIG. 1. The specific preparation methods were as follows:
I. Protein Production
1. Plasmid Extraction
200 ul bacteria solution was inoculated into mLYT medium containing 50 ug/ml ampicillin. After 6 hours of incubation at 37° C. on a shaker, the deposit was collected via centrifugation. The deposit was resuspended with 12 ml RES buffer, mixed well, and 12 ml LYS lysis buffer was added, mixed well by inversion and placed at room temperature for 2 min. 12 ml of NEU neutralization solution was added and immediately mixed by inversion. 35 ml of EQU buffer was added into an equilibration column containing filters. Buffer was added on the edge of the filter membrane to ensure that the entire filter membrane was wet. After filtered through gravity, EQU was added into the inverted and mixed lysis solution to prevent clogging of the filter. The filter was washed with 10 ml EQU. After the liquid in the column had flowed through, the equilibrated column was inverted and the filter membrane was discarded. The column was washed a first time with 90 mL of Endo buffer. The column was washed a second time by adding another 45 ml of Wash buffer after the liquid had flowed through. Additional 45 ml of ELU buffer was added to the column, and the eluate was collected into a 50 ml centrifuge tube. Plasmid DNA was precipitated by adding 10.5 ml of isopropanol at room temperature, mixing, and standing at room temperature for 5 min. The solution was filtered with a filter membrane, and the filter membrane was washed with 5 ml of 70% ethanol. After complete removal of ethanol from the filter, 1 ml of water was added to the filter to dissolve DNA in a 1.5 ml cryovial. The extracted plasmids were sequenced.
2. Expression of 3G11-scFv and FMC63-scFv Proteins
FMC63 is a traditional anti-CD19 CAR and 3G11 is a mutated anti-CD19 CAR (See patent Application Number CN201710357213.3).
1.5 mg each of KL20629-2 and KL20743-1 plasmids were transfected into 293-6E cells using PEI method. Cells were cultured at 37° C. in roller bottles for 7 days and collected for antibody purification.
3. Purification of 3G11-scFv and FMC63-scFv Antibodies
The cell culture products 3G11 scFv FC and FMC63 scFv FC were centrifuged. The supernatant was collected and filtered with sartopore2 (Sartorius) to remove cell debris, and the filtered clear solution was collected. The target protein was purified and collected by using 10 ml of Mab-select SuRe. The collected target protein was concentrated by centrifugation at 30K with 15 ml of Centrifugal Filter Units, then filtered using Millex-GP Filter Unit (0.22 μm, sterile). The affinity yields were determined separately by using the NanoDrop2000 assay for A280. The target protein was further purified over a 440 ml Superdex200 zeolite column. The primary target protein was collected according to the peak output and filtered through a Millex-GP Filter Unit (0.22 μm, sterile). The final antibody yields were determined separately using the nanodrop2000 assay for A280. The final product quality was analyzed by QC using SDS-PAGE, SEC-HPLC, and LAL methods.

II. Mouse Immunization and Serum Titer Detection

1. Hock Immunization
The amount of antigen administered to each mouse was 10 ug, and the antigen: TiterMax adjuvant ratio was 1:1. Hock immunizations were performed to 10 BALB/c mice in groups 2-3 and 10 SJL mice in groups 5-6. The antigen was then emulsified. The capsule silver mercury regulator was switched on, and an 1.5 ml centrifuge tube containing the mixture of antigen, adjuvant and PBS were put into it. The mixture was vortexed and emulsified until it was completely emulsified into the water-in-oil state. The mixture of emulsified antigen and adjuvant was aspirated into a 1-ml sterile syringe. The ankle parts of both feet of the mice were disinfected by wiping with a 75% alcohol cotton ball, and the syringe needle tips were beveled upward, with the graduated face toward the operator, and the needle was advanced parallel to the ankle so as to e slowly inject the mixture of antigen and adjuvant. At least 2 h observation was performed after the completion of immunization.
2. Immunization with Intraperitoneal Injection
The amount of antigen required for the immunization was calculated according to immunization procedures. The antigen:adjuvant ratio was 1:1, and antigen was diluted with PBS into corresponding concentrations as required. 5 BALB/c mice of group 1 and 5 SJL mice of group 4 were immunized intraperitoneal (i.p.). The antigen was then emulsified. The capsule silver mercury regulator was switched on, and an 1.5 ml centrifuge tube containing the mixture of antigen, adjuvant and PBS were put into it. The mixture was vortexed and emulsified until it was completely emulsified into the water-in-oil state. The mixture of emulsified antigen and adjuvant was transferred into a 2-ml sterile syringe. Air bubbles were exhausted. The mouse tail was grasped with right hand and the skin of the head and neck was gently grasped with thumb and index finger of the left hand. The abdominal cavity was up and the injection site on right abdominal of the mouse was wiped with a 75% alcohol cotton ball. The tip of the syringe needle that had previously aspirated the antigenic drug was beveled upward and the head of the mouse was downward. The syringe was punctured into the skin in parallel and into the abdominal cavity of the mouse with an angle of 45 degree from the abdominal cavity. The mixture of antigen and adjuvant was slowly injected. At least 4 h observation was performed after the completion of immunization.
3. Collection of Mouse Serum
The corresponding serum tube number of each mouse was marked and the mouse ear peg number was checked. The mouse was grasped with single hand and approximately 200 ul of whole blood was taken through the mouse facial submandibular vein. After standing at room temperature for approximately 1 h, the collected whole blood sample was centrifuged to collect the upper serum of the centrifuge tube. The serum was stored at 4° C. freezer within a week for relevant experimental detection such as antibody titer. For long-term preservation, the serum was maintained at −80° C. and prevented from repeated freeze-thaw cycles.

4. ELISA Serum Titer Assay in Immunized Mice

Before the start of the experiment, the 96-well plate was correspondingly marked and coated with 50 ul antigen of 1 ug/ml concentration per well in refrigerator at 4° C. overnight. Next day, the antigen plate coated the day before yesterday was taken out and washed with washing machine once (washing buffer: 1×PBST). After washed, the antigen plate was blocked for 1 hour at 37° C. in 1% BSA blocking solution prepared with 1×PBST. The plate was washed 3 times with 1×PBST wash solution, then different diluted concentrations of the serum to be examined were added and incubated for 1 hour at 37° C. in the incubator. The plate was washed 3 times with 1×PBST wash solution, then sheep-anti-mouse secondary antibody was added. The plate was incubated for 0.5 hours at 37° C. in the incubator, washed and color was developed using the mixture of TMB color development solution A liquid and B liquid at ratio of 1:1. After 15 min, the color development was stopped with 1N hydrochloric acid. Fluorescence values at 450 nm were detected on a Spectra Max M5 multi-purpose plate reader.

5. FACS Serum Titer Assay in Immunized Mice

After the CART and PBMC cell suspensions were centrifuged and the cells was resuspended in PBS containing 0.1% BSA and counted. The serum to be tested from each group of immunized mice was added. The cells were washed three times after incubation for 40 min at room temperature and then added with Anti-Mouse IgG (Fc specific)-FITC secondary antibody. Then the cells were washed three times after incubation for 30 min in the dark and at room temperature. The cells were gently resuspended with PBS containing 0.1% BSA, and detected on the machine.

III. Fusion and Screening of Hybridoma Cells

1. PEG Fusion Technology

SP2/0 cells were screened for rejuvenation one week prior to fusion and expanded by cultured in 10% DMEM medium. The spleen and lymph nodes were removed from the sacrificed mice in a biological safety cabinet, rinsed and ground in a culture dish, mixed and collected into a 50 ml centrifuge tube, and centrifuged at 1000 rpm for 5 min to remove the supernatant. SP2/0 cells after the expanded culture were collected into a 50 ml centrifuge tube and centrifuged at 1000 rpm for 5 min to remove the supernatant. SP2/0 cells and lymphocytes were respectively counted after resuspension with serum-free DMEM medium. SP2/0 cells were counted by Count star cell automated counter, and lymphocytes were counted by using a blood count plate. SP2/0 cells and lymphocytes were mixed at a ratio of 1:4, and centrifuged at 1000 rpm to remove the supernatant. The cells were flicked and 1.5 ml of 37° C. pre-warmed PEG was added in one minute at a uniform speed and mixed while adding. The cells were placed for 1.5 min. Then the fusion was stopped with DMEM containing 15% FBS. After standing for 5 min, the supernatant was removed by centrifugation at 1000 rpm for 5 min. Splenocytes were adjusted into a concentration of $0.5 \times 10^6$ cells/ml with 20% FBS DMEM medium containing 1×Hat, and added into 96-well plates at 200 μL/well. The 96-well plates were incubated in a incubator at 37° C., 5% $CO_2$, and the cell status was observed daily. The fusion rate of cells was counted after fusion for 5 days. The fused hybridoma cells were screened after fusion for 9-14 days, and the positive cells were picked and expanded in 24-well plates.

2. Electrofusion Technique

SP2/0 cells were screened for rejuvenation one week prior to fusion and expanded by cultured in 10% DMEM medium. The spleen and lymph nodes were removed from the sacrificed mice in a biological safety cabinet, rinsed and ground in a culture dish, mixed and collected into a 50 ml centrifuge tube, and centrifuged at 1000 rpm for 5 min to remove the supernatant. 2 ml of red blood cell lysing solution was added, and after lysing 3 min at 4° C., DMEM medium with 10% FBS was added to 50 ml to terminate red lysis. SP2/0 cells and lymphocytes in a good state were respectively collected and centrifuged in a 50 ml centrifuge tube to remove supernatant, then counted after resuspension with serum-free DMEM medium. SP2/0 cells were counted by Count star cell automated counter, and lymphocytes were counted by using a blood count plate. SP2/0 cells and lymphocytes were mixed at a ratio of 1:2, and centrifuged at 1000 rpm to remove the supernatant. Cells were resuspended and mixed in 10 ml of incubated Cytofusion Medium C and washed 3 times, and then resuspended in 6 ml of Cytofusion Medium C. The electrofusion instrument was switched on for fusion according to the set procedure. The fused cells were spread in 96-well plates and incubated in an incubator at 37° C., 5% $CO_2$, and the cell status was observed daily. The fusion rate of cells was counted after fusion for 5 days. The fused hybridoma cells were screened after fusion for 9-14 days, and the positive cells were picked and expanded in 24-well plates.

3. Subcloning Fusion Cells by Limiting Dilution

HT medium with 15% FBS was formulated, and cell lines to be subcloned were resuspended from 24-well culture wells and counted separately using a Countstar IC1000 cytometer. The cell concentration of each cell strain was diluted into 5-10 cells/ml with 20 ml of configured HT medium. The diluted cell suspension was added to 15 cm disposable Petri dishes and to 96-well culture plates with 0.2 ml per well and 1-2 cells per well. The cells spread in 96-well plates were incubated in a incubator at 37° C., 5% $CO_2$. After 7-10 days, the subclone plates were detected and screened according to the growth of cells, and positive clones were picked up and placed into 24-well plates for further positive confirmation.

4. ELISA Screening of Fusion Cells

1) Coating with Antigen a) Two clean 250 ml low sorption liquid storage bottles were prepared and marked with relevant information (e.g., project number, sample name, concentration, date, and operator, etc.) in advance as that on the 96-well ELISA plate.

b) 12.5 ml of 20×PBS was added into two liquid storage bottles respectively, and 237.5 ml of ddH₂O was added to dilute it into 1×PBS.

c) From the sample tube, 200 ul of 3G11-scFv-hFc (1.25 mg/ml) was added to one liquid storage bottle and 161.3 ul of NC scFv HFC (1.55 mg/ml) to the other, and shaken separately, thereby forming a solution of a final concentration of 1 ug/ml.

d) The above solutions were added to the corresponding 96-well ELISA plate respectively as soon as possible, and put into the 4° C. freezer for overnight incubation.

2) Washing Plates a) 250 ml of 20×PBS was taken to a specific container of 5 L and diluted into 5 L of 1×PBS solution by adding 4750 ml of ddH₂O.

b) 2.5 ml of Tween 20 was added to prepare 1×PBST wash solution containing 0.05% Tween 20 (1×PBS+0.05% Tween20).

c) The prepared 1×PBST solution was well mixed and added into the liquid storage bottles corresponding to plate washers for subsequent use.

d) The condition of plate washer was checked to make sure that the instrument functioned correctly without any clogging.

e) The coated ELISA plates were washed once with 300 ul/well of 1×PBST using the appropriate wash procedure of the plate washer.

f) The instrument condition was checked again after all washes were completed to ensure the that was no clogging, then the appropriate maintenance procedure was initiated.

3) Blocking a) 50 ml of 20×PBS was taken to a marked 1 L liquid storage bottle and diluted into 1 L of 1×PBS solution by adding 950 ml of ddH$_2$O.

b) 10.00 g of BSA was weighed with a balance and added into the liquid storage bottle and shaken well until fully dissolved.

c) 500 ul of Tween 20 was aspirated and added into the above solution, mixed to obtain the blocking solution and dilution buffer. It was prepared by this method (1×PBS+0.05% Tween20+1% BSA) if needed in subsequent processes.

d) The blocking solution was added to the ELISA plate with 250 ul/well, incubated in an incubator at 37° C. for 1.5 hours. After completion of blocking, the blocking solution was discarded. The blocked ELISA plate may be stored at −20° C.

4) Adding Primary Antibodies a) The blocked ELISA plates were thawed in an incubator at 37° C. and washed once. The ELISA plates were marked with information according to the clone number on corresponding fusion plates.

b) Two tubes of 1 ml hybridoma cell culture medium of the same stage was taken. 1.00 ul of FB was added into one tube as a positive control sample and the other tube of culture medium was used as a negative control sample.

c) The hybridoma supernatant from the fusion plates was taken into the corresponding ELISA microwell plate with the standard volume of 50 ul/well, and 50 ul of the negative and positive control samples were respectively added into the reserved well.

d) The above ELISA detection plates were incubated in an incubator at 37° C. for 1 h and then washed by a plate washer.

5) Washing Plates a) The condition of plate washer was checked to make sure that the instrument functioned correctly without any clogging. The PBST solution can be prepared as mentioned in step 2) if it was insufficient.

b) The coated ELISA plates were washed 3 times with 300 ul/well of 1×PBST using the appropriate wash procedure of the plate washer.

c) The instrument condition was checked again after all washes were completed to ensure the that was no clogging, then the appropriate maintenance procedure was initiated.

6) Adding Secondary Antibodies a) 100 ml of dilution buffer prepared in the step 3 "Blocking" were added with 20 ul of Anti-Mouse IgG (Fc specific)-HRP (1:5000). The above secondary antibody solution was added into the cleaned ELISA detection plate with 50 ul per well.

b) The plates were incubated in an incubator at 37° C. for 0.5 h and then washed by a plate washer.

7) Washing Plates a) The condition of plate washer was checked to make sure that the instrument functioned correctly without any clogging. The PBST solution was prepared as mentioned in step 2) "Washing plates" if it was insufficient.

b) The coated ELISA plates were washed 3 times with 300 ul/well of 1×PBST using the appropriate wash procedure of the plate washer.

c) The instrument condition was checked again after all washes were completed to ensure the that was no clogging, then the appropriate maintenance procedure was initiated.

8) Color Development a) The cleaned ELISA plates were separated according to different coating samples, and ordered by the clone number.

b) TMB color development solution was prepared at a 1:1 ratio in a clean container, by mixing and shaking 90 mL each of liquid A and liquid B.

c) The prepared TMB color development solution was added into the ELISA detection plate in a volume of 100 ul per well for color development (15 minutes).

9) Terminating a) 880 ml of ddH$_2$O was added into the designated reagent bottle and additional 80 ml of hydrochloric acid (AR.36-38%) was taken and diluted in advance under the fume hood to obtain 1N of hydrochloric acid solution for use, which was prepared using the same method if needed in subsequent processes (the original concentration was 12N).

b) The color development was terminated by adding 1N of HCl to the ELISA detection plate in a volume of 50 ul per well.

10) Plate Reading a) Information such as plate or clone number corresponding to the ELISA plate was typed on the microplate reader software in advance, plates were sequentially placed and checked carefully during reading procedure;

b) After the color development was terminated, the plate reading analysis was performed at a wavelength of 450 nm using a microplate reader immediately. The required data results were exported, and saved or uploaded to the designated location.

5. FACS Screening of Fusion Cells

1) Collecting Cells a) 100 ul of cell culture solution was collected for cell counting.

b) The cell culture solution with the required cell amount for each experiment was taken and centrifuged at 1000 rpm for 5 min in a centrifuge, and the supernatant was discarded.

c) Cells were resuspended (viable cell concentration of $1.02 \times 10^6$ cells/ml) in an equal proportion FACS buffer (1×PBS+2% FBS) for plating.

2) Plating a) According to the number of samples, 100 ul of cell suspension of step 1) was added into each of the corresponding wells. (The final viable cell count was $1.02 \times 10^5$ per well)

b) After blocking for 20-30 min at room temperature, the samples were centrifuged at 300 g for 5 min at 4° C., and the supernatant was discarded.

3) Adding Primary Antibodies
  a) Hybridoma supernatants or control samples were taken to the corresponding microplates according to the standard volume of 100 ul/well and cells were resuspended.
  b) The above detection plates were incubated in an incubator at 4° C. for 1 h and then washed with FACS buffer.
4) Washing Plates
  a) Cells were resuspended by adding 200 ul/well of FACS buffer, centrifuged at 300 g for 5 min at 4° C., and the supernatant was discarded.
  b) The above washing step was repeated.
5) Adding Secondary Antibodies
  a) 3 ml of FACS buffer was taken and 3 ul of Anti-Mouse IgG (Fc specific)-Alexa488 (1:1000) was added.
  b) The above secondary antibody solution was added into the cleaned detection plate according to the standard volume of 100 ul per well.
  c) The plates were transferred to freezer and incubated at 4° C. in the dark for 1 hour, and then washed twice with FACS buffer.
6) Washing Plates
  a) 200 ul/well of FACS buffer was added, centrifuged at 300 g for 5 min at 4° C., and the supernatant was discarded.
  b) The above washing step was repeated.
7) Detecting
  a) The cells from step 6 were resuspended with 100 ul of 1×PBS and kept in the dark for analysis.

IV. Production, Purification and Labeling of Specific Antibodies

1. Antibody Production and Purification
The culture medium 2.5% SFM (SFM medium containing 2.5% ultra low IgG FBS, 1×Pen-Strep solution) for antibody production was prepared. Cells required for antibody production were observed microscopically until growing to ≥70% confluency and in good cell condition. Cells were collected and counted with Countstar IC1000 cytometer. The cell concentration was adjusted to 1~5×10$^5$ cells/ml and transferred to Roller Bottle. Roller bottle of the transferred cells was placed in the roller bottle incubator and cultured at 37° C. for 10-15 days. The growth condition of the cells was observed daily. When the medium became orange and transparent, it was removed for purification.
2. Antibody Purification by Passing Cell Supernatants Through a Protein a Column
3. Labeling Antibodies with Biotin
Biotin-NHS was dissolved in anhydrous DMF to prepare 10 mg/ml DMF solution for use. The antibody to be labeled was taken and placed into two 15 ml centrifuge tubes, and the concentration of the antibody was measured using the IgG working mode of UV-Nanodrop. The antibody was added with biotin-NHS (concentration of 10 mg/ml), reacted in a water bath at 25° C. for 30 min, and then added with 1 M aqueous ammonium chloride solution to terminate the reaction, respectively. The biotin conjugated antibody was placed into a dialysis bag and dialyzed overnight in 1×PBS buffer at 4° C. Dialysate was changed once 4 h after the first dialysis. On the morning of the third day of the experiment, biotinylated antibody sample was taken from the dialysis bag and placed into two clean 15 ml centrifuge tubes. The sample concentration was measured by using the BCA protein concentration assay kit. The biotin labeling results were verified with ELISA method.

The monoclonal antibodies of the present invention may also be labeled using other methods well known in the art.

V. Detection of Monoclonal Antibody Characteristics

1. Identification of Monoclonal Antibody Subclasses
The monoclonal antibody subclass kit instructions were followed and antigen mediated ELISA was used. The cell culture supernatant was added separately to the plates coated with antigen with 50 μL/well, incubated at 37° C. for 1 h, washed with PBST three times for 5 min each time, and added with 1:1000 dilution of goat-anti-mouse IgG$_1$, IgG$_{2a}$, IgG$_{2b}$, IgG$_3$, and IgM subtype antibodies (50 μL/well), and incubated at 37° C. for 0.5 h. 2 wells were tested for each monoclonal antibody and each subclass, wherein the wells were washed with PBST three times for 5 min each time; added with 1:5000 dilution of rabbit-anti-goat enzyme labeled second antibody (50 μL/well), incubated at 37° C. for 15 min, washed with PBST three times; added with chromogenic solution o-phenylenediamine (OPD) solution (50 μL/well). Color development was performed for 10~15 min at 37° C. in the dark and terminated by adding 2 m H$_2$SO$_4$ (50 μL/well). The subclass antibodies added to the wells whose color was significantly higher than that in other wells under naked eye observation were monoclonal antibody subclasses.

The result of detection shows that the amino acid sequence of the complementarity determining region 1 (CDR1) of the light chain variable region of the monoclonal antibody (marked as 3984-mab001-H) is shown in SEQ ID NO: 1, and specifically is: RASQDISNYLN.

The amino acid sequence of the complementarity determining region 2 (CDR2) of the light chain variable region of the monoclonal antibody is shown in SEQ ID NO: 2, and specifically is: YTSRLRS.

The amino acid sequence of the complementarity determining region 3 (CDR3) of the light chain variable region of the monoclonal antibody is shown in SEQ ID NO: 3, and specifically is: QQGDTLPYT.

The amino acid sequence of the light chain variable region of the monoclonal antibody is shown in SEQ ID NO: 4 as follows:

```
DIQMTQTTSSLSASLGDRVTISCRASQDISNYLNWYQQKPDGTVKLLIY

YTSRLRSGVPSRFSGSGSGADYSLTISNLEQEDIATYFCQQGDTLPYTF

GGGTKLEIN.
```

The amino acid sequence of the complementarity determining region 1 (CDR1) of the heavy chain variable region of the monoclonal antibody is shown in SEQ ID NO: 5, and specifically is: GYSFTDY.

The amino acid sequence of the complementarity determining region 2 (CDR2) of the heavy chain variable region of the monoclonal antibody is shown in SEQ ID NO: 6, and specifically is: DPYNGG.

The amino acid sequence of the complementarity determining region 3 (CDR3) of the heavy chain variable region of the monoclonal antibody is shown in SEQ ID NO: 7, and specifically is: TYDNYEFAY.

The amino acid sequence of the heavy chain variable region of the monoclonal antibody is shown in SEQ ID NO: 8 as follows:

EIQLQQSGPELVKPGASVKVSCKASGYSFTDYTMYWVKQSHGKSLEWIG

YIDPYNGGTNYSQRFKGKATLTVDKSSSTAFMHLNSLPSEDSAVYYCAN

TYDNYEFAYWGQGTLVTVSA 5

Example 2 Preparation of Antibody

The nucleotide sequences encoding the light and heavy chains of monoclonal antibody 3984-mab001-H were synthesized according to SEQ ID NO: 4 and SEQ ID NO: 8. The heavy chain cDNA and light chain cDNA of monoclonal antibody 3984-mab001-H were linked with a linking peptide (GGGGSGGGGSGGGGS, SEQ ID NO: 11) and cloned into pCMV vector, thereby the recombinant expression plasmid of monoclonal antibody 3984-mab001-H was obtain.

The recombinant plasmid was transfected into HEK293F cells. Hek293F cell culture supernatant was collected and detected after affinity purification. The monoclonal antibody 3984-mab001-H was obtained.

Example 3 Assembly of CAR-T Cell Detection Kit

The assembly steps of CAR-T cell detection kit were as follows:
(1) Preparation of Biotin-Labeled Monoclonal Antibody (Designated as Bio-3984-Mab001-H):
    The monoclonal antibody 3984-mab001-H obtained in Example 2 was labeled by standard biotin labeling method to obtain biotin-labeled monoclonal antibody Bio-3984-mab001-H. 2-10 mg of monoclonal antibody Bio-3984-mab001-H protein was dissolved in 1 ml of phosphate buffer, and concentration in millimole of the dissolution was calculate. Biotin was equilibrated to room temperature. 2 mg Sulfo-NHS-Biotin was added into 100 μL ultrapure water, then added with a certain concentration of biotin, placed at room temperature for 30 min, or on ice for 2 h. The column was prewashed with 30 ml PBS, loaded with the sample and the same buffer according to the amount to be collected. 0.5 ml or 1 ml solution was collected into a separate tube for determination of monoclonal antibody protein content according to absorbance at 280 nm.
(2) Kit Assembly
    Microporous membrane plates (e.g., 96-well filter plates), biotin-labeled monoclonal antibody Bio-3984-mab001-H and other components were placed into the plastic holder of the kit according to the number of bottles loaded in each kit. The kits were packaged and assembled. The instructions were put into the kits and the outer and side labels were labeled.
    Further, one or more of the dilutions, washing solution (20×), blocking solution, negative control (e.g., complete 1640 medium), and positive controls (FMC63 scFv recombinant protein or IgG) were assembled into the kits.
    In the kid, the microporous membrane plate and the biotin-labeled monoclonal antibody Bio-3984-mab001-H could be replaced by a microcellular membrane plate coated with biotin-labeled monoclonal antibody Bio-3984-mab001-H.
    The method for preparing the microcellular membrane plate coated with biotin-labeled monoclonal antibody Bio-3984-mab001-H was as following:
    (1) The sterile 96-well filter plate was opened. PVDF membrane was pre-wetted for 1 min by using 35% ethanol (20 μl/well), then washed three times with PBS (250 μL/well) for 1 min each time.

(2) 5 μg/ml of biotin-labeled monoclonal antibody Bio-3984-mab001-H was added to the 96-well membrane plate with 100 μL/well and coated overnight at 4° C.
    (3) The coating solution was discarded, and plates were washed 3 times for 1 min each time using water containing sterilized PBS;
    (4) Complete 1640 medium supplemented with 10% fetal bovine serum was added with 200 μL/well, and incubated at 37° C. for 2 h for blocking.
    (5) The blocking solution was discarded, the plates were washed once by using PBS, dried at 37° C. for 2 h. Desiccant was added and placed into a sealing bag together with the 96-well membrane plates, vacuum sealed, and stored at 4° C.

TABLE 1

| No. | Reagent | Amount |
|---|---|---|
| | Components of kits involved in the invention | |
| 1. | 96-well microporous membrane plate (microcellular membrane plate of biotin-labeled monoclonal antibody Bio-3984-mab001-H) | 1 |
| 2 | Positive control (FMC63 scFv recombinant protein or IgG) | 10 μL |
| 3 | Negative control (complete 1640 culture medium) | 10 μL |
| 4 | Dilution | 22 mL |
| 5 | Washing solution (20 x) | 30 mL |
| 6 | Specification | 1 |

Example 4 the Effects of the Monoclonal Antibody of Invention on Detecting Expression of Anti-CD19 CAR 1. Experimental Materials:
    1) Control group: a commercial product purchased from ACROBiosystems, model CD19-H8259.
    Initial experimental method for control product: CD19 CAR-T cells (the extracellular binding domain of the CAR was FMC63scfv) were resuscitated and added with 100 μl Biotinylated Human CD19, Fc Tag (5 μg/ml) and incubated for 20 min at room temperature, then added with 5 μL PE anti-Biotin, incubated for 20 min in the dark and at room temperature, washed once, and detected by flow cytometry (Cytoflex).
    Optimized experimental method for control product: CD19 CAR-T cells (the extracellular binding domain of the CAR was FMC63scfv) were resuscitated and added with 100 μl Biotinylated Human CD19, Fc Tag (10 μg/ml) and incubated for 1 h at 4° C., then added with 5 μL PE anti-Biotin, incubated for 20 min in the dark and at room temperature, washed 3 times, and detected by flow cytometry (Cytoflex and Attune).
    2) Experimental group: anti-CD19 scFv antibody of the present invention: CD19 CAR-T cells (the extracellular binding domain of the CAR was FMC63scfv) were resuscitated and added with the biotin-labeled monoclonal antibody Bio-3984-mab001-H from the kit prepared in Example 3 of the present invention, stained for 20 min, added with 5 μL PE anti-Biotin, incubated for 20 min in the dark and at room temperature, washed once, and detected by flow cytometry (cytoflex and attune).
    Three parallel sets of experiments were set up for each group.

Figure 2:
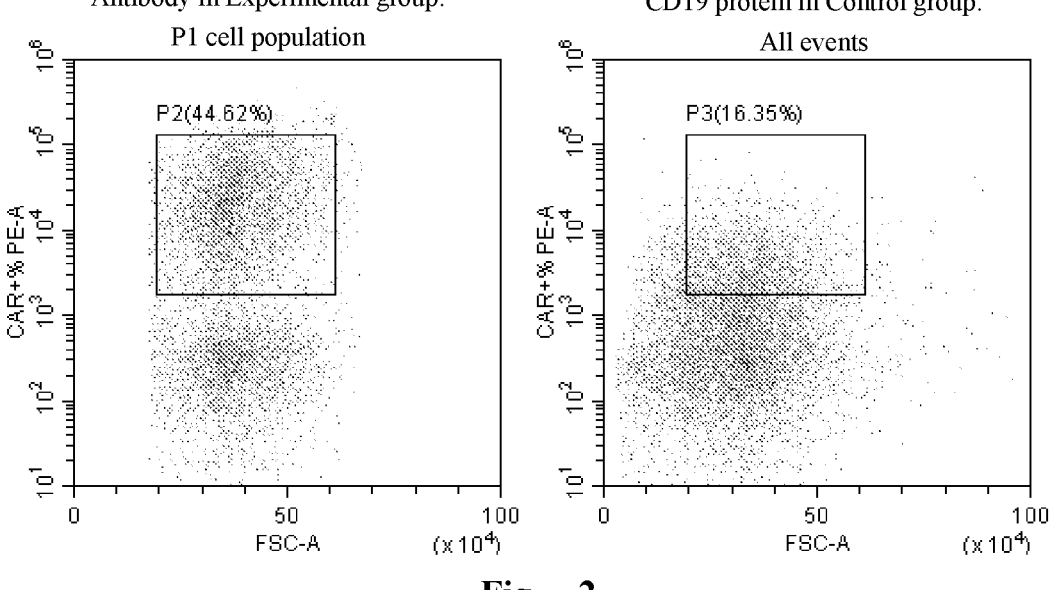
FIG. 2 shows a plot illustrating the specific CytoFlex detection results of the antibody in the experimental group and CD19 protein in the control group for binding antiCD19 CAR-T cells as compared in an example of the present invention. Among them, the left figure is experimental group, the right figure is control group, and the lower figure is homotype control group.
Figure 2:
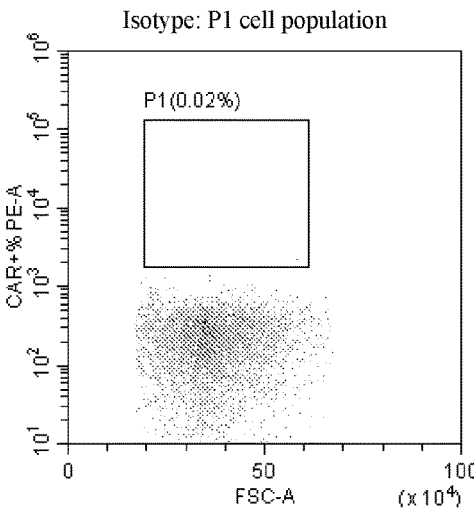
Figure 3:
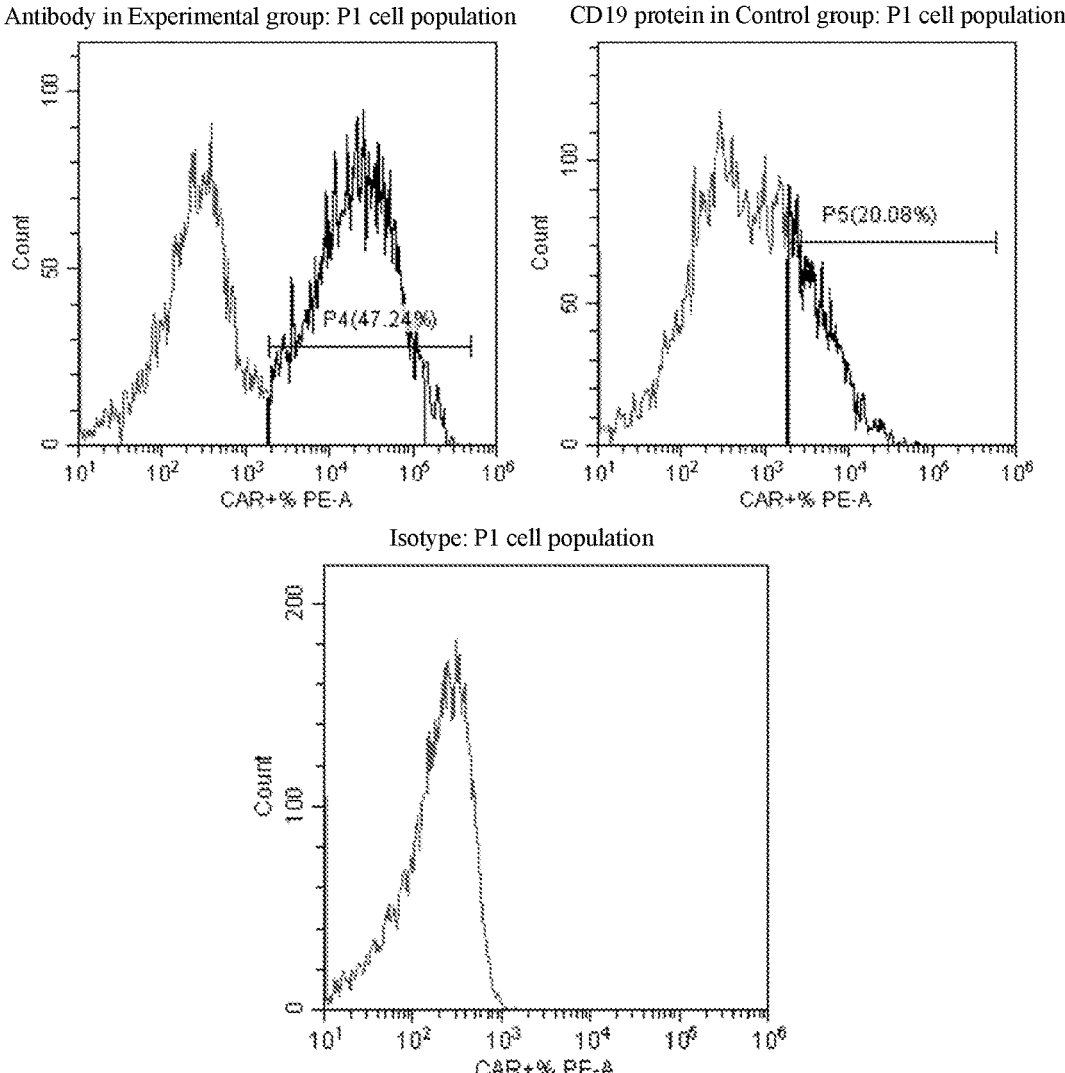
FIG. 3 shows a histogram illustrating the specific CytoFlex detection result of antibody in the experimental group and CD19 protein in the control group for binding antiCD19 CAR-T cells as compared in an example of the present invention. Among them, the left figure is experimental group, the right figure is control group, and the lower figure is homotype control group.
Figure 4:
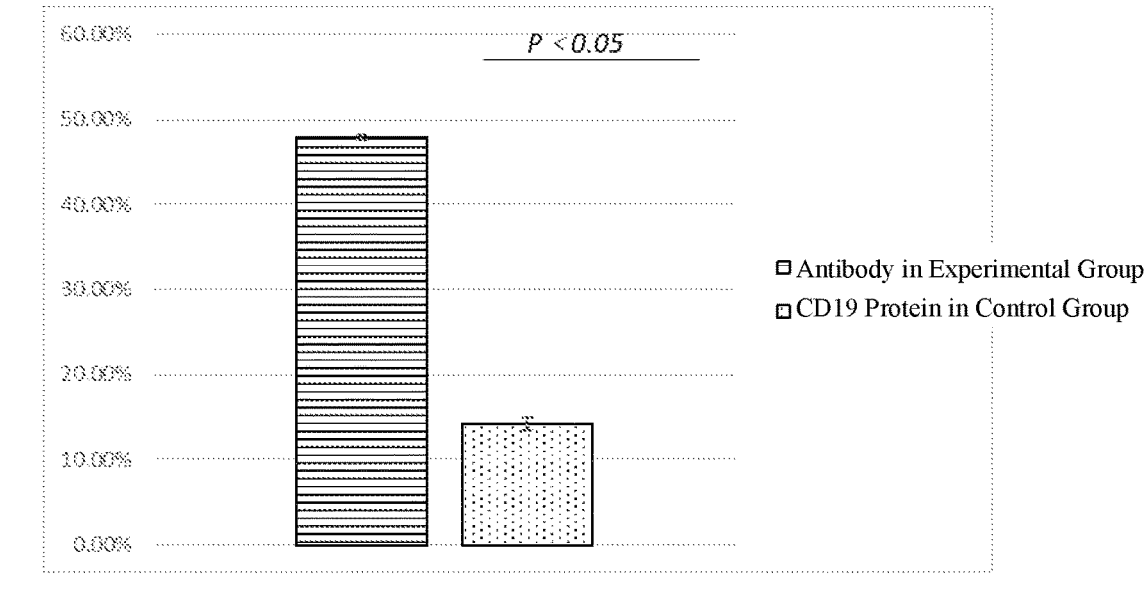
FIG. 4 shows an average result of three measurements of the specific CytoFlex detection of antibody in the experimental group and CD19 protein in the control group for binding antiCD19 CAR-T cells in an example of the present invention.

2. Experimental Results:

As shown in FIGS. 2-4 and summarized in Table.2, CD19 antigen protein failed to stably detect anti-CD19 CAR expression on the surface of CD19 CAR-T cells (14.24±5.15%, RSD=36.20%), while the anti-CD19 scFv antibody of the present invention was capable of stably detecting anti-CD19 CAR expression (47.88±0.65%, RSD=1.35%), P=0.004.

TABLE 2

| Antibody | CAR % | P |
|---|---|---|
| Experimental group antibody(3984-mab001) | 47.86% | 0.0004 |
| Experimental group antibody(3984-mab001) | 48.53% | |
| Experimental group antibody(3984-mab001) | 47.24% | |
| Control group CD19 protein | 10.34% | |
| Control group CD19 protein | 12.29% | |
| Control group CD19 protein | 20.08% | |

Example 5 Monoclonal Antibody of the Invention could Efficiently Block CD19 CAR-T Cells CD19 CAR-T cells (the extracellular domain of the CAR was FMC63 scFv) were blocked by using 25 μg/ml and 5 μg/ml of the monoclonal antibody of the present invention (mAb 3984-mab001-H prepared in Example 2), and subsequently detected for the killing effect on CD19-K562 cells or CD19$^+$K562 cells at effector:target ratios of 1:1 and 5:1. The ratio of the killed cell was calculated specifically by detecting the release of LDH.

Figure 5:
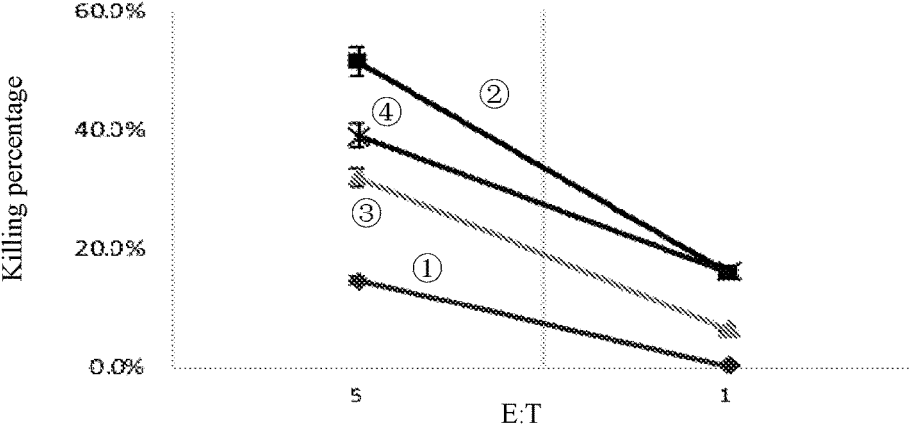
FIG. 5 shows the killing of the target cell after blocking the CAR-T cell with the monoclonal antibody of the present invention.

The results are shown in FIG. 5 and Table.3. When the effector:target ratio was 5:1 and the antibody concentration was 5 μg/ml, the monoclonal antibody of the present invention significantly inhibited the killing of CD19$^+$K562 cells by CAR-T cells, with the killing rate decreasing from 51.5% to 39.1%. The killing rate could further decrease to 32% when the antibody concentration increased to 25 μg/ml. Moreover, when the effector:target ratio was 1:1 and the antibody concentration was 25 μg/ml, the monoclonal antibody of the present invention could further reduce the killing rate from a low level 16.0% to 6.5%. The above results indicated that the monoclonal antibody of the present invention, even at a low concentration, exhibited excellent blocking effect on CD19 CAR-T cells and inhibited the killing effect of CAR-T cells, which illustrated that the monoclonal antibody of the present invention could specifically recognize scFv fragments of CD19 CAR and had excellent detection sensitivity.

TABLE 3

| | Killing of target cells after blocking CAR-T cells with the monoclonal antibody | | | |
|---|---|---|---|---|
| | Killing rates in each group | | | |
| Effector: Target ratio — | CAR-T + K562 PARENTAL | CAR-T + CD19$^+$K562 WITHOUT mAb | CAR-T + CD19$^+$K562 WITH mAb 25 μg/ml | CAR-T + CD19$^+$K562 WITH mAb 5 μg/ml |
| 5 | 14.7% | 51.5% | 32.1% | 39.1% |
| 1 | 0.1% | 16.0% | 6.5% | 16.1% |

In contrast, in the same detection, the currently known antibody against the FMC63 scFv failed to block the killing effect of the targeted CD19 CAR-T cells (the extracellular binding domain of the CAR was FMC63 ScFv) with a dosage of 5 μg/ml and a effector:target ratio of 5:1. The monoclonal antibody of the present invention has higher sensitivity and better blocking performance and, therefore it is more suitable for detecting the killing performance of CAR-T cells in which the extracellular binding domain of CAR is FMC63 ScFv, and for quality control.

The above examples are to illustrate the embodiments disclosed by the present invention and should not be construed as limitations to the invention. Furthermore, the various modifications listed herein, as well as variations in methods and compositions in the invention, are apparent to those skilled in the art without departing from the scope and spirit of the invention. While the present invention has been specifically described in combination with multiple specific preferred examples of the present invention, it should be understood that the present invention should not be limited to these specific examples. In fact, various modifications of the technical solutions described above that would be obvious to a person skilled in the art should all be included within the scope of the invention.

The invention claimed is:

1. A monoclonal antibody specifically binding to a chimeric antigen receptor (CAR) molecule, which comprises a light chain and a heavy chain, wherein the light chain and the heavy chain comprise light chain variable regions (VL) and heavy chain variable regions (VH) which comprise the complementarity determining regions (CDR), wherein the light chain variable region comprises a VL CDR1 having an amino acid sequence as shown in SEQ ID NO: 1, a VL CDR2 having an amino acid sequence as shown in SEQ ID NO: 2, and a VL CDR3 having an amino acid sequence as shown in SEQ ID NO: 3, and the heavy chain variable region comprises a VH CDR1 having an amino acid sequence as shown in SEQ ID NO: 5, a VH CDR2 having an amino acid sequence as shown in SEQ ID NO: 6, and a VH CDR3 having an amino acid sequence as shown in SEQ ID NO: 7.

2. The monoclonal antibody specifically binding to a CAR molecule according to claim 1, which comprises one or more of the following features:

1) the light chain variable region has an amino acid sequence as shown in SEQ ID NO: 4; and the heavy chain variable region has an amino acid sequence as shown in SEQ ID NO: 8;

2) the monoclonal antibody is murine-derived;

3) the monoclonal antibody is a subtype selected from the group consisting of IgG1, IgG2a, IgG2b, IgG2c and IgG3.

3. The monoclonal antibody specifically binding to a CAR molecule according to claim 1, wherein the light chain variable region has an amino acid sequence as shown in SEQ ID NO: 4.

4. The monoclonal antibody specifically binding to a CAR molecule according to claim 1, wherein the heavy chain variable region has an amino acid sequence as shown in SEQ ID NO: 8.

5. The monoclonal antibody specifically binding to a CAR molecule according to claim 1, wherein the light chain variable region has an amino acid sequence as shown in SEQ ID NO: 4 and the heavy chain variable region of the monoclonal antibody has an amino acid sequence as shown in SEQ ID NO: 8.

* * * * *